(12) United States Patent
Vines

(10) Patent No.: US 6,901,345 B1
(45) Date of Patent: May 31, 2005

(54) VACUUM EXTRACTION MONITOR FOR ELECTRIC PUMP

(76) Inventor: Victor L. Vines, 7242 Brookcove, Dallas, TX (US) 75214

( * ) Notice: Subject to any disclaimer, the term of this patent is extended or adjusted under 35 U.S.C. 154(b) by 49 days.

(21) Appl. No.: 09/727,006

(22) Filed: Nov. 30, 2000

(51) Int. Cl.[7] .............................................. G06F 15/00
(52) U.S. Cl. ...................................... 702/138; 606/123
(58) Field of Search ......................... 702/138; 606/123, 606/205, 119, 120; 118/715, 724; 73/714

(56) References Cited

U.S. PATENT DOCUMENTS

| | | | |
|---|---|---|---|
| 2,831,478 A | | 4/1958 | Herbert et al. |
| 3,062,215 A | | 11/1962 | Heyns |
| 3,112,749 A | | 12/1963 | Sokol |
| 4,014,344 A | | 3/1977 | Gutierrez |
| 5,277,557 A | | 1/1994 | Cooper |
| 5,298,021 A | | 3/1994 | Sherer |
| 5,395,379 A | | 3/1995 | Deutchman et al. |
| 5,569,265 A | * | 10/1996 | Elliott ......................... 606/123 |
| 5,649,934 A | | 7/1997 | Smeltzer et al. |
| 5,982,274 A | | 11/1999 | Stetler et al. |
| 6,074,399 A | | 6/2000 | Wallace et al. |
| 6,289,737 B1 | * | 9/2001 | Kouketsu et al. ............. 73/714 |
| 6,299,691 B1 | * | 10/2001 | Oda et al. .................... 118/715 |
| 6,355,047 B1 | | 3/2002 | Wallace et al. |
| 6,361,542 B1 | * | 3/2002 | Dimitriu et al. ............ 606/119 |

FOREIGN PATENT DOCUMENTS

| | | | | |
|---|---|---|---|---|
| BE | 755 528 A | | 2/1971 | |
| DE | 11 14 278 B | | 9/1961 | |
| DE | 23 47 850 A | | 4/1975 | |
| DE | 87 11 729 U | | 11/1987 | |
| GB | 839 327 A | | 6/1960 | |
| JP | 405215633 A | * | 8/1993 | ........... G01L/21/00 |
| JP | 05269086 A | * | 10/1993 | ............ A61B/5/00 |
| WO | WO 00 32115 A | | 6/2000 | |
| WO | WO 00 32123 A | | 6/2000 | |

OTHER PUBLICATIONS

01287951 EMBASE No: 1979008445, Title: Controlled vacuum extraction by measuring the pressure exercised by the truss Author(s): Meyenburg M.; Hein H.W. Geburtsh. Abt., Frauenklin., Freie Univ., Berlin Germany.*
Source: Zeitschrift fur Geburtshilfe and Perinatologie (Z. Geburtshilfe Perinatol.) (Germany) 1978, 182/5 (381–383), Coden: ZGPRA, Document Type: Journal.*
Glenn A. Hunt, Master ASE Technician (www.mityvac-.com), [on–line], [retrieved on Jan. 13, 2003].*
www.mityvac.com.
www.prismenterprise.com.
http://www.prismenterprise.com/mityvacob/mityvac.html.
Bestgen et al: "Force and Pressure Measurement During Vacuum Extractions in Obstetrics".
Reports in Applied Measurement, Hottinger Baldwin Messtechnik, Darmstadt, DE, vol. 9, No. 1, 1995, pp. 1–4. XP000521570 ISSN: 0930–7923 The Whole Document.
Rule 39.1 (iv) PCT—Method for Treatment of the Human or Animal Body by Surgery.

* cited by examiner

Primary Examiner—John Barlow
Assistant Examiner—Xiuqin Sun
(74) Attorney, Agent, or Firm—Thrasher Associates, LLC

(57) ABSTRACT

The present invention aids a person who is assisting with fetal extraction by monitoring and recording the pressure inside a vacuum device. In one embodiment, the invention is a pump-attachable device for monitoring and recording a pressure in a vacuum device that includes an adapter enabled to attach to a pressure gauge receiver of an electric pump, and a cable coupled to the pressure transducer which in enabled to attach to a monitor for recording a detected pressure. In yet another embodiment, the invention is a method of using a recording device for recording a pressure in a vacuum device. The invention includes coupling a monitor to the vacuum device, calibrating the monitor, and recording the pressure to produce a record.

18 Claims, 6 Drawing Sheets

VACUUM EXTRACTION MONITOR FOR ELECTRIC PUMP

RELATED APPLICATIONS

The present invention is related to co-filed and co-pending U.S. patent application Ser. No. 09/727,124, entitled Vacuum Extraction Monitor with Attachment For Hand Pump by Dr. Victor Vines, and co-filed and co-pending U.S. patent application Ser. No. 09/727,123, entitled Vacuum Extraction Monitoring, by Dr. Victor Vines. All of which were filed on Nov. 30, 2000.

TECHNICAL FIELD

The invention relates to childbirth, and more specifically, the invention relates to vacuum extraction deliveries. More particularly still, the invention relates to systems, devices, and methods for monitoring vacuum extraction deliveries.

STATEMENT OF A PROBLEM ADDRESSED BY THIS INVENTION

When operative vaginal deliveries are necessary, there are presently two options—forceps extraction, or vacuum extraction. Vacuum extraction in labor/delivery suites has become a well-accepted and commonly performed form of vaginal delivery because it may be less hazardous to the mother and fetus than forceps extraction. However, there is the potential for harm to the fetus from forceps extraction. However, there is the potential for harm to the fetus from prolonged suction application to the fetal head. In addition, there are guidelines governing the amount of vacuum pressure that should be applied to the fetal head, as well as guidelines regarding the duration of time that the vacuum pressure is applied to the fetal head during vacuum extraction (these guidelines are printed by the manufacturers of vacuum devices, and are also available in medical literature).

Exemplary effects of vacuum extraction on an infant during delivery include: fetal hypoxia, retinal hemorrhage, chignon-scalp marking and abrasion, cephalhematoma and subcutaneous hematoma, neonatal jaundice, intra-cranial hemorrhage, shoulder dystocia, and subgaleal hemorrhage. Subgaleal hematoma is a particularly dangerous condition. Subgaleal hematoma is formed when bleeding occurs into the potential beneath the aponeurosis of an infant's scalp. It may be a life threatening condition for a newborn baby, and is often considered the most serious complication associated with the vacuum extraction. One danger associated with subgaleal hematoma arises because the subaponeurotic space stretches over the whole part of the cranial vault of the infant, and a large proportion of the baby's blood volume can accumulate in this space (typically, from damage to the emissary veins). Although subgaleal hematoma may occur after forceps and natural deliveries, the incidents of subgaleal hematoma is increased considerably in vacuum extractions since the introduction of the vacuum device pulls the aponeurosis from the cranium and may injure the underlying veins. Furthermore, because hemorrhaging into the subgaleal space may occur slowly, and for several hours following delivery, bleeding into the subgaleal space may be difficult to initially detect.

Accordingly, there are occasions when a fetus does poorly during and after vacuum extraction. Often, a legal claim is made against a doctor, hospital, nurses, and others associated with the delivery, alleging that the guidelines regarding the use of the vacuum device were not followed.

Other complications involved with using vacuum devices include attention being diverted away from the delivery process itself when attention is given to the vacuum pressure being applied to the fetal head. Furthermore, large amounts of activity by different personnel who participate in the delivery may create confusion and chaos in which the monitoring of a vacuum pressure in the vacuum device goes undocumented. The present invention provides a solution that overcomes these and other disadvantages associated with the prior art.

SELECTED OVERVIEW OF SELECTED EMBODIMENTS

In one embodiment, the invention is a method of using a vacuum recording device for recording a pressure in a vacuum device. The invention includes detecting pressure in the vacuum device, recording the pressure in the vacuum device, and storing the pressure in the vacuum device.

Alternatively, the invention may be practiced as a method of using a vacuum recording device for recording a pressure in a vacuum device. The invention applies a suction device to a fetus, initiates a vacuum pressure in the suction device, detects the vacuum pressure in the suction device, and automatically records the vacuum pressure in the suction device.

In another embodiment, the invention is a pump-attachable device for monitoring and recording a pressure in a vacuum device. The invention includes an adapter enabled to attach to a pressure gauge receiver of an electric pump, an air pressure detector secured in the adapter such that the pressure detector is exposed to an air cavity in the electric pump, and a cable coupled to the pressure transducer which in enabled to attach to a monitor for recording a detected pressure.

In yet another embodiment, the invention is a method of using a recording device for recording a pressure in a vacuum device. The invention includes coupling a monitor to the vacuum device, calibrating the monitor, and recording the pressure to produce a record.

BRIEF DESCRIPTION OF THE DRAWINGS

Various aspects of the invention, as well as an embodiment, are better understood by reference to the following EXEMPLARY EMBODIMENT OF A BEST MODE. To better understand the invention, the EXEMPLARY EMBODIMENT OF A BEST MODE should be read in conjunction with the drawings in which.

AN EXEMPLARY EMBODIMENT OF A BEST MODE

The invention allows physicians to measure and record the amount of pressure and the duration of pressure applied to a fetus' head during vacuum extraction, and the invention lowers litigation costs because a permanent record of vacuum pressures applied during delivery is created. Accordingly, the invention provides systems, devices, and methods for aiding a person who is assisting with fetal extraction. The invention is attachable to a vacuum device, and may incorporate a vacuum device. Furthermore, the pressure inside the vacuum device is monitored and recorded by a recording device.

Figure 1:
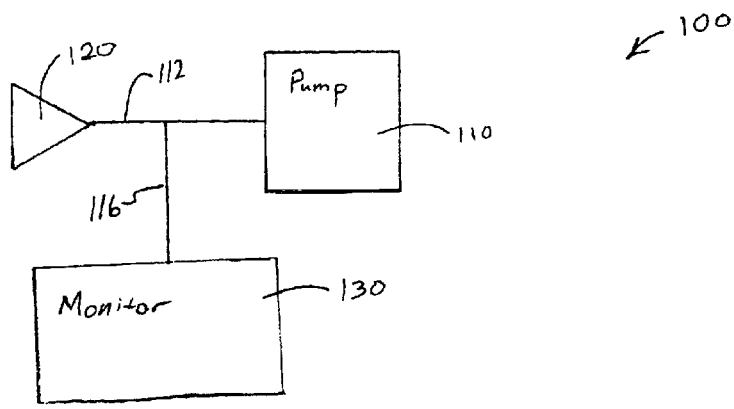
FIG. 1 provides a block diagram of a vacuum device, illustrating systems incorporated by the invention.

Preferably, the invention provides at least the features of monitoring and recording pressures in a suction device used for vacuum-based fetal extraction. Accordingly, FIG. 1 provides a block diagram of a vacuum device 100, illustrating systems incorporated by the invention. A pump 110 which could be a manually activated hand pump, an electric pump, or any other type of air pump, is fluidly coupled to a suction device 120. The suction device 120 is attachable to a fetus, being preferably attachable to fetal head. The suction device 120 is preferably a cup, such as a SILC, a SILASPIC, a SOFT-CUP, or a MALMSTROM cup, for example. Fluid coupling between the suction device 120 and the pump 110 may be accomplished by a tube 112, and is preferably a plastic tube.

A recording device 130, which may be a monitor, an enhanced monitor, or a custom-developed device for example, provides a user the ability to monitor air pressures and record air pressures. Accordingly, air pressures may be measured in the monitor 130, or in the tube 112, or in the pump 110. Furthermore, in FIG. 1, a cable 116 couples the tube 112 to the monitor 130. Accordingly, in this embodiment, an air pressure is detected in the tube 112 and converted into information by a device such as a transducer. Next, the detected pressure is passed as information along the cable 116 to the monitor 130.

Figure 2:
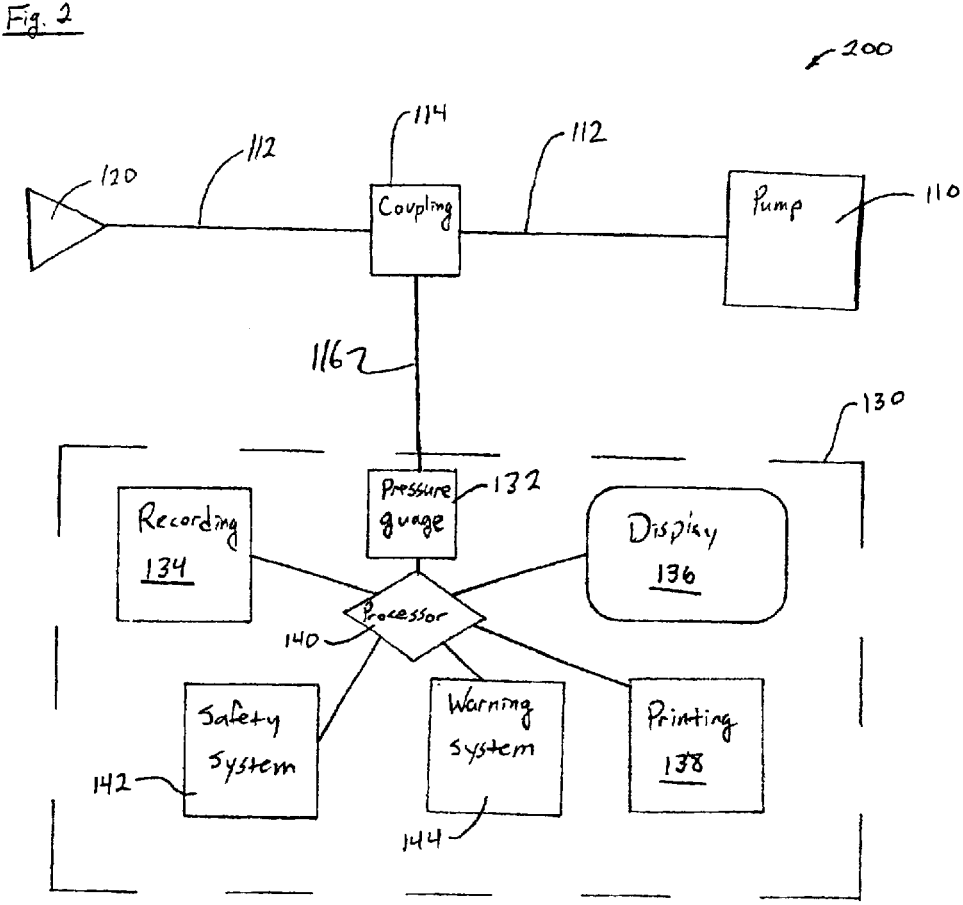
FIG. 2 provides a more detailed block schematic of a vacuum device.

With an initial understanding of the vacuum device 100, one may gain a better understanding of the invention by referring to a more detailed block schematic. Accordingly, FIG. 2 provides a more detailed block schematic of a vacuum device 200. The vacuum device 200 has a pump 110 in fluid communication with the suction device 120 through a tubing 112. The tubing 112, although not illustrated, may contain therein a wire for coupling the pump 110 to the suction device 120 (to provide a device which may support traction tension between the pump 110 and the suction device 120). A coupling 114 is shown dividing the tubing 112. However, it should be understood that the coupling 114 need not be intrusive of the tubing 112, and could be embodied as a cap/tap, for example. In any event, the coupling is enabled to detect the pressure in the tubing (whether the pressure is actually detected in the tubing 112, the suction device 120, or the pump 110). Preferably, the coupling 114 is a plastic tube with a transducer therein. Although not shown in FIG. 2, a transducer in the coupling detects a pressure, and then produces a mechanical or electrical signal based on the pressure detected. or other transportable signal based on the detective pressure such as a wireless radio frequency communication).

The cable 116 provides a commutative connection between the coupling 114 and a pressure gauge 132 located in the recording device 130. Of course, although the pressure gauge 132 is illustrated as being located in the recording device 130, the pressure gauge 132 could in fact be located in the coupling 114, or along the cable 116. Thus, the pressure gauge 132 functions as a mechanical or electrical signal receiver which translates a mechanical signal, or electrical signal, or a wireless signal into data that is associated with a pressure.

A processor 140 was coupled to the pressure gauge 132, and provides a means for processing data from the pressure gauge 132 and associating that data with various tables, algorithms, and other information. Furthermore, processor 140 may drive other systems such as a display 136, a printing device 138, warning system 144, or a safety system 142, or send information to a recording device 134. Preferably, the processor is a digital signal processor (DSP), a Pentium processor, or a Strong Arm processor, for example. The processor 140 retrieves various tables, algorithms, and other information from the recording device 134, that preferably stores an electronic record. Preferably, the recording device 134 is embodied as memory, such as RAM, ROM, or removable memory such as Flash RAM, a Memory Stick, or a CD ROM.

The display 136 provides real time information, such as pressures over time, dangerous conditions detected (or other information) to persons assisting with the extraction of the fetus. Preferably, the display 136 is a cathode ray video screen, or a plasma screen.

The printing device 138 provides the ability to print numbers or graphs indicating a pressure over time, progressive pressures detected over time. Preferably, the printing device 138 generates these prints on paper. Furthermore, although illustrated as being integrated into the recording device 130, it should be understood that the printing device 138 may be located externally from the recording device 130.

The safety system 142 causes the implementation of a safety pressure release valve preferably located on the pump 110. When triggered, the safety system 142 may release some of the pressure, or all of the pressure thus returning the pressure inside the tubing 112 to the local atmospheric pressure (or room pressure). The safety system 142 may be embodied as software algorithm for execution in memory, or as mechanical device.

The warning system 144 is for producing a warning when a predetermined pressure or pressures are detected. Typically, the predetermined pressure will be a vacuum pressure which is lower than a predetermined vacuum pressure, such as 0.2 kgms/cm$^2$–0.8 kgms/cm$^2$, depending on the stage of delivery. The warning may be embodied as a light, a sound, or a voice, for example. A light may flash at different rates, or present different colors, or present different intensities as pressure changes in the tube. Similarly, a sound may change in tone as different pressures are detected, or a voice may verbally indicate a pressure or a warning condition. Furthermore, the warning system may be used to trigger and provide information to the safety system 142.

Figure 3:
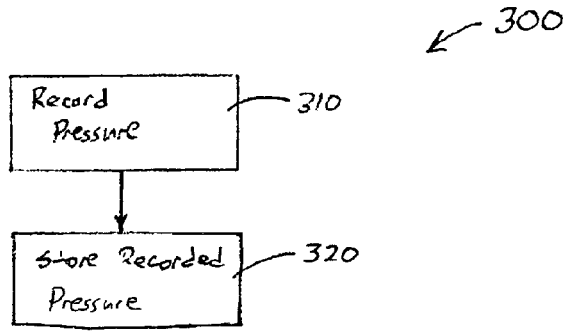
FIG. 3 provides a flowchart of a recording algorithm which illustrates one embodiment of the invention.

A better understanding of the invention may be achieved by examining the operation of the invention. FIG. 3 provides a flowchart of a recording algorithm 300. First, in a record pressure act 310, the recording algorithm 300 records a pressure which exists in a vacuum device. Then, in a store recorded pressure act 320, the recording algorithm 300 creates a permanent record of the pressure which was recorded in the record pressure act 310.

Figure 4:
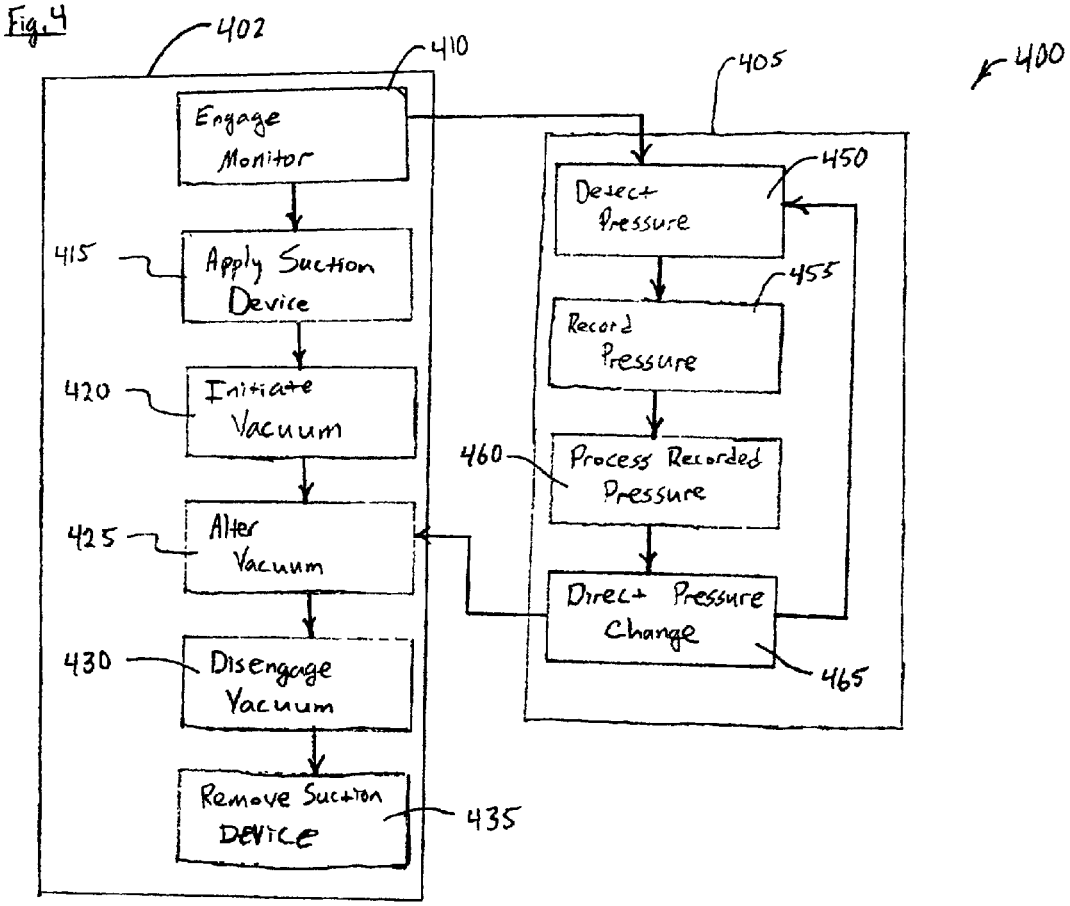
FIG. 4 illustrates a block flow diagram of a vacuum device algorithm that implements one embodiment of the invention.

An even better understanding of the invention may be realized by examining the processes flow of a vacuum device embodied according to the invention. Accordingly, FIG. 4 illustrates a block flow diagram of a vacuum device algorithm 400 that implements one embodiment of the invention. The vacuum device algorithm 400 comprises a pump algorithm 402 for illustrating acts performed with a vacuum device pump, and a monitor algorithm 405 illustrating acts associated with a recording device. The vacuum device algorithm 400 begins in a pump algorithm 402.

The pump algorithm 402 is initiated in an engage monitor act 410. The engage monitor act may include attaching a cable between a vacuum pump and a recording device, and then turning on the recording device. After the engage monitor act 410, the pump algorithm 402 proceeds to an apply suction device act 415 in which a suction device is attached to a fetus, and preferably a fetal head. It should be noted that in the apply suction device act 415, if a disposable MITYVAC is being used in the procedure, adapters should be attached to suction tubing of the vacuum device and the disposable MITYVAC assembly. After the suction device is applied to the fetus, the apply suction device act 415 proceeds by calibrating, or zeroing, the monitor so that the pressure detected prior to applying a vacuum to the fetus is recognized as being the local atmospheric pressure.

Following the apply suction device act 415, the pump algorithm 402 proceeds to an initiate vacuum act 420. In the initiate vacuum act 420 a vacuum pressure is created in the vacuum device by manually actuating a manual pump, or by engaging the vacuum switch or trigger in an electric pump. The next act in the pump algorithm 402 change, the vacuum pressure (which is initiated in response to a command to change the pressure in the vacuum device). This is accomplished in an altervacuum pressure act 425, and is typically employed as a result of a response received from the monitor algorithm 405. Of course, altering the vacuum pressure may not be necessary during a vacuum extraction procedure, and thus the alter vacuum pressure act 425 should especially be viewed as an optional act for the present embodiment (although the only needed acts are explicitly articulated in the claims).

Next, a disengage vacuum act 430 is performed when the pressure in the vacuum device is returned to at least local atmospheric pressure. Furthermore, the pressure may be raised to a pressure greater than local atmospheric pressure to encourage the suction device to separate from the fetus. Then, the vacuum device algorithm 400 and pump algorithm 402 end together in a remove suction device act 435, in which the suction device is removed from the fetus. Furthermore, in the remove suction device act 435 the recording device may be disengaged, and the record of the pressures detected during the vacuum device algorithm 400 may be stored in a permanent medical record, which may be a physical paper record and/or an electronic record.

The monitor algorithm 405 initiates in a detect pressure act 450, which begins in response to the initialization of the recording device in the engage monitor act 410. In the detect pressure act 450 a pressure in the vacuum device is detected, which will typically be between a room (or atmospheric) pressure and vacuum pressure (meaning a pressure lower than the local atmospheric pressures). Next, the vacuum device algorithm 400 continues to a record pressure act 455. In the record pressure act 455 the pressure detected in the detect pressure act 450 is automatically recorded (or stored), preferably by an electronic means (such as a memory) or by a paper means. Furthermore, the record pressure act 455 may include the displaying of the recorded pressure on a monitor or other display.

The recorded pressures are monitored and processed in a process recorded pressure act 460. The process recorded pressure act 460 evaluates the detected pressure in a warning system, and may direct the displaying or printing of additional information in response to the warning system. [The process-recorded pressure 460 may include a sub-act of displaying the processed information on the display device, such as a monitor.] Likewise, if the process is recorded at 460 determines if the detected pressure exceeds a predetermined pressure, the process recorded pressure act 460 may direct a pressure change, such as a lower pressure, or an immediate return to local atmospheric pressure, in a direct pressure change act 465. The direct pressure change act 465 produces the electrical or mechanical signals needed to implement the alter-vacuum pressure act 425.

The intention provide the ability to accurately measure, record, and trace pressure event that transpire in a vacuum device during vacuum extraction. Accordingly, the invention assist physicians, hospitals, and other delivery personnel in the defense of accusation that proper guidelines were not followed during the vacuum extraction. Furthermore, those who suffer from improper vacuum extraction also have access to a permanent medical record which should facilitate mediated settlements, and avoid the costs of lengthy discovery and emotionally scaring litigation. Also, because data will be collected with each vacuum extraction, the guidelines for the conduct of a vacuum extraction may be changed and improved to more accurately be able to predict safe guidelines for a vacuum extraction delivery.

Figure 5:
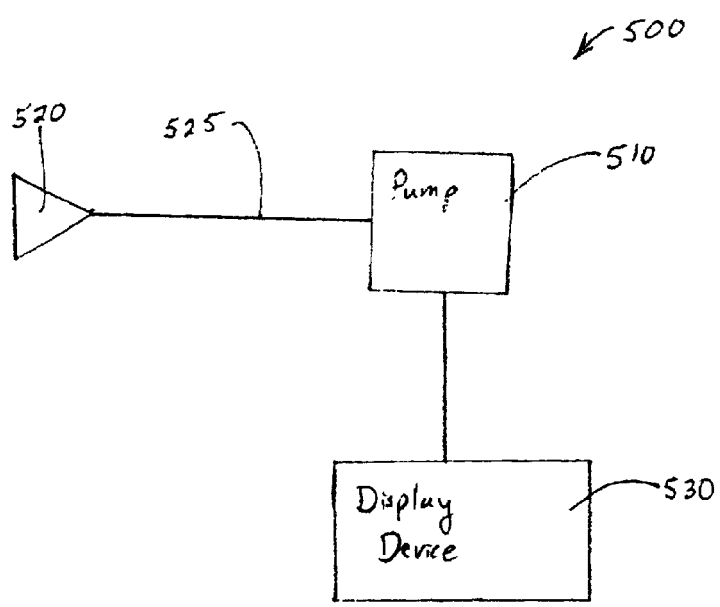
FIG. 5 provides a block diagram of an adapter assembly which provides existing vacuum devices the features of the invention, and is accordingly another embodiment of the invention.

It will sometimes be advantageous to provide existing vacuum devices the ability to access the advantages provided by the invention. FIG. 5 provides a block diagram of an adapter assembly 500 which provides existing vacuum devices access to advantages of the invention, and is accordingly another embodiment of the invention. The adapter assembly 500 comprises a pump 510 fluidly coupled to a suction device 520 by a tubing 525. A display device 530 is connected to the pump 510. Preferably, the display device 530 is coupled to the pump 510 via an adapter to the pump 510. Better understanding of the adapter assembly 500 may be achieved by examining specific embodiment.

Figure 6:
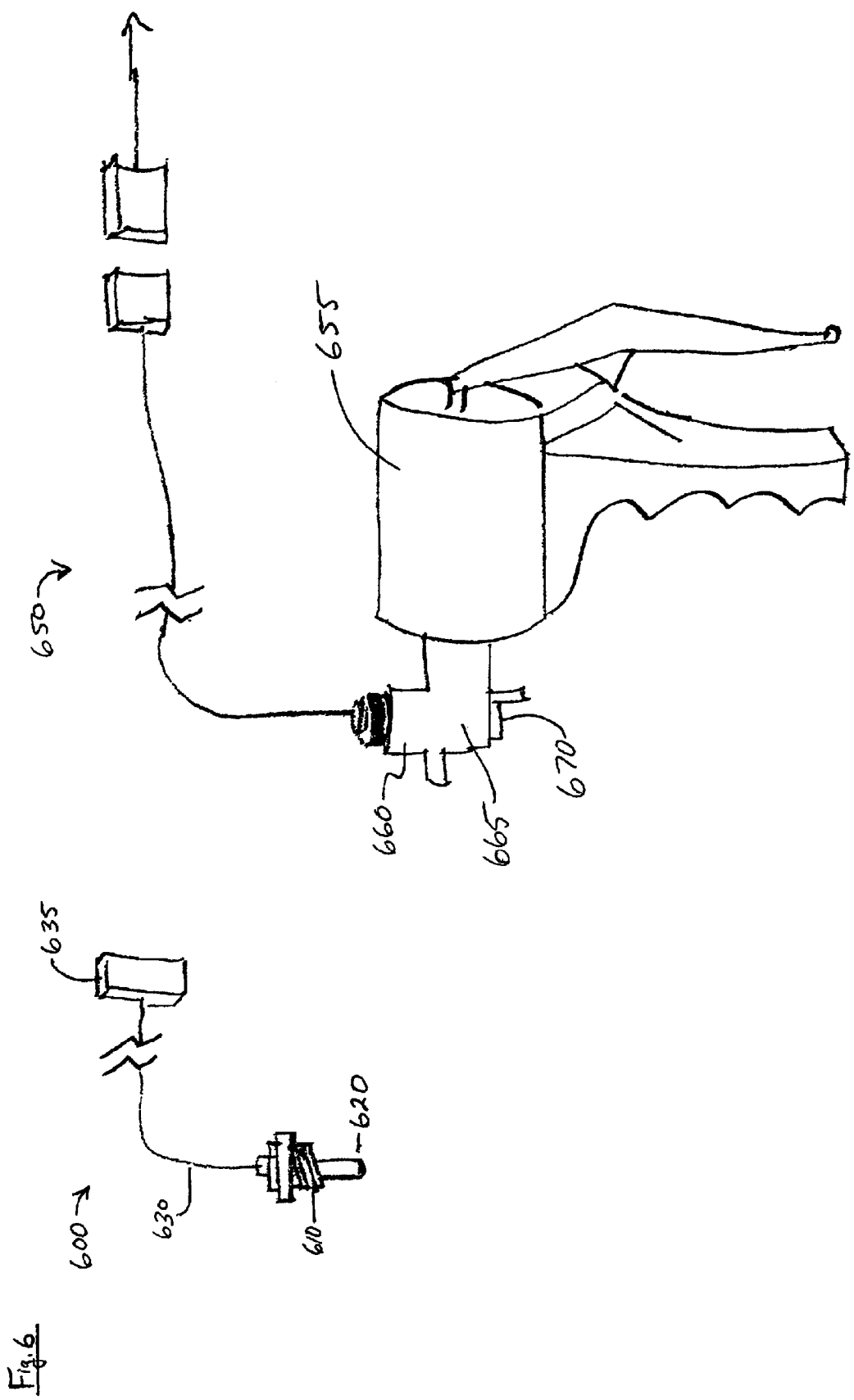
FIG. 6 illustrates a pump attachable device capable of attachment to an electrical pump.

FIG. 6 illustrates a pump attachable device 600 capable of attachment to an electrical pump 655. The pump attachable device 600 has an adapter 610, such as the threaded fittings illustrated in FIG. 6. Furthermore, the pump attachable device 600 has a pressure transducer 620 which detects a pressure and converts the detected pressure to a mechanical or electrical signal capable of being transferred to a monitor (not shown) via a cable 630. The cable 630 includes a plug 635 capable of attachment to a monitor or other recording device.

Also, illustrated in FIG. 6 is a pump system 650 having a pump attachable device attached thereto. The pump system 650 includes an electric pump 655 such as a MITYVAC, or disposable MITYVAC, for example. The electric pump 655 has a front end 665 which has a cavity for supporting other devices and for transporting the pressures, including the vacuum pressure, created by the electric pump 655.

The front end 665 has thereon a pressure gauge receiver 660. Typically, the pressure gauge receiver 660 accepts a pressure gauge that mechanically detects a pressure which is then displayed for those performing the vacuum procedures. In operation of one embodiment of the invention, the pressure gauge is removed from the electric pump, typically by unscrewing the pressure gauge, and the pump attachable device 600 is then inserted into the pressure gauge receiver 660. Also provided by the front end 665 is a pressure release valve 670. The pressure release valve 670 allows the inflow of air into the front end, and particularly into the cavity of the front end, in order to increase the pressure in the vacuum device.

Figure 7:
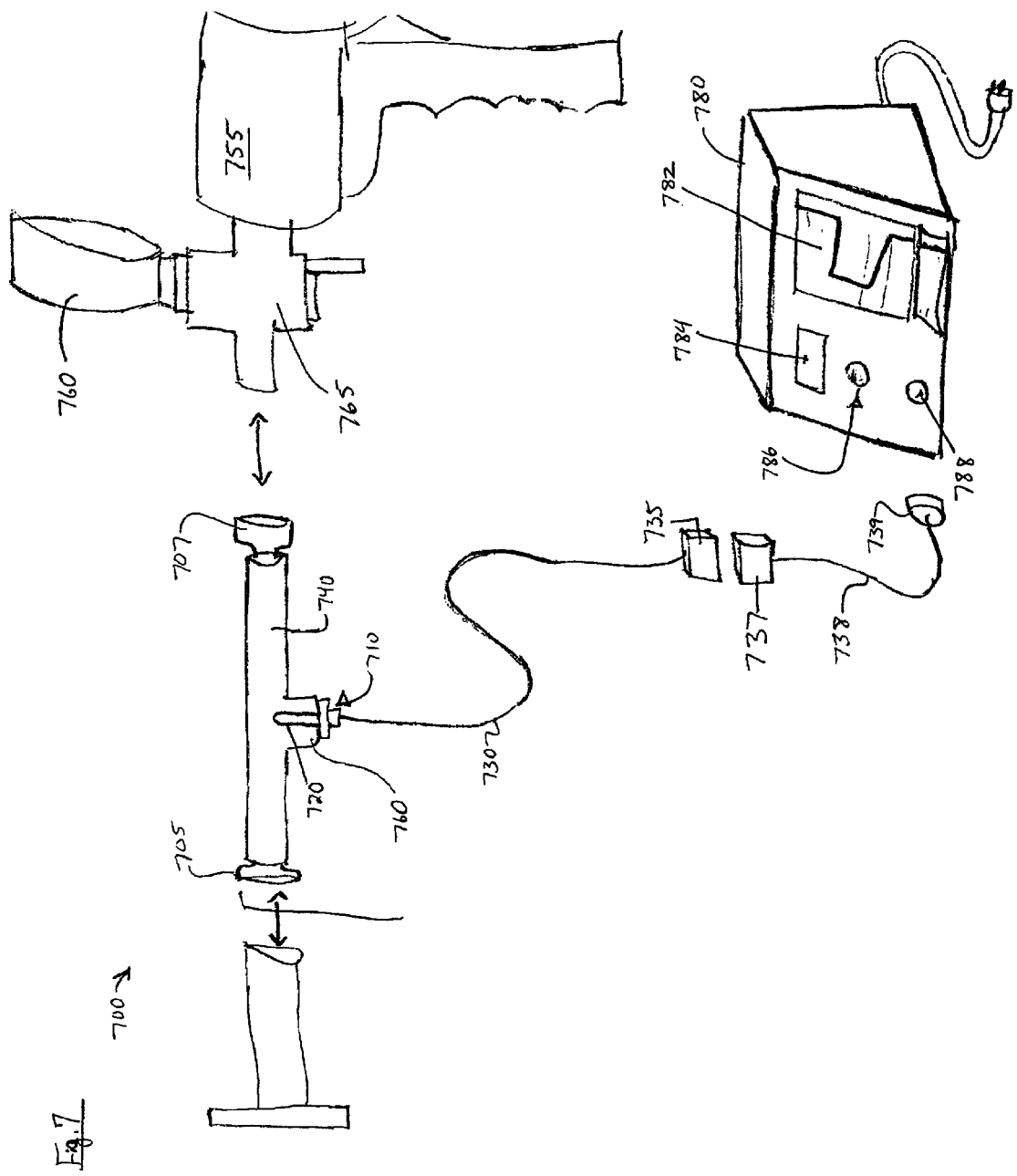
FIG. 7 as a tube attachable device.

Another embodiment of the invention is illustrated in FIG. 7 as a tube attachable device 700. The tube attachable device 700 includes a first end 705, and a second end 707. The first end 705 is preferably configured to either attach to a plastic tube section, or a suction device. The second end 707 is preferably configured to attach to a tube, or a front end such as the front end 765 that is adapted to receive the second end 707. The tube attachable device 700 includes tubing 740, which is preferably plastic tubing.

The tubing 740 includes a pressure gauge receiver 760. Accordingly, a transducer/pressure gauge 720 is inserted into the tubing 740 and secured in the tubing by an adapter 710. Furthermore, pressures detected by the pressure transducer 720 are converted into a data signal that is sent to a recording device along a cable 730. The cable 730 also includes a plug 735 which is connectable to the recording device monitor 780, or to a second plug 737. The plug 737 couples an extension cord 738 to a second plug 739. The second plug 739 is also attachable to the recording device 780 at a plug socket 788.

The vacuum device illustrated in FIG. 7 includes a pump 755, which provides a disposable MITYVAC, and a pressure gauge 760 which is fitted into the front end 765. Thus, the vacuum device provides a physician the advantage of having a mechanical visual display provided by the gauge 760 (thus requiring little change by those who are accustom to viewing the mechanical gate 760), as well as providing mechanical and electric displays and printouts of the recorded pressures while the recording device 780.

The recording device 780 may produce a printed-paper record 782, as well as a visual display 784. Of course, the printed-paper record 782 or the visual display 784 may print or display numbers, graphical representation or other indicia of the pressures being detected in the vacuum device. Furthermore, the recording device 780 provides a warning device 786 which could produce a light, sound, or a vocalized recording of a warning to those assisting with the fetal extraction.

Figure 8:
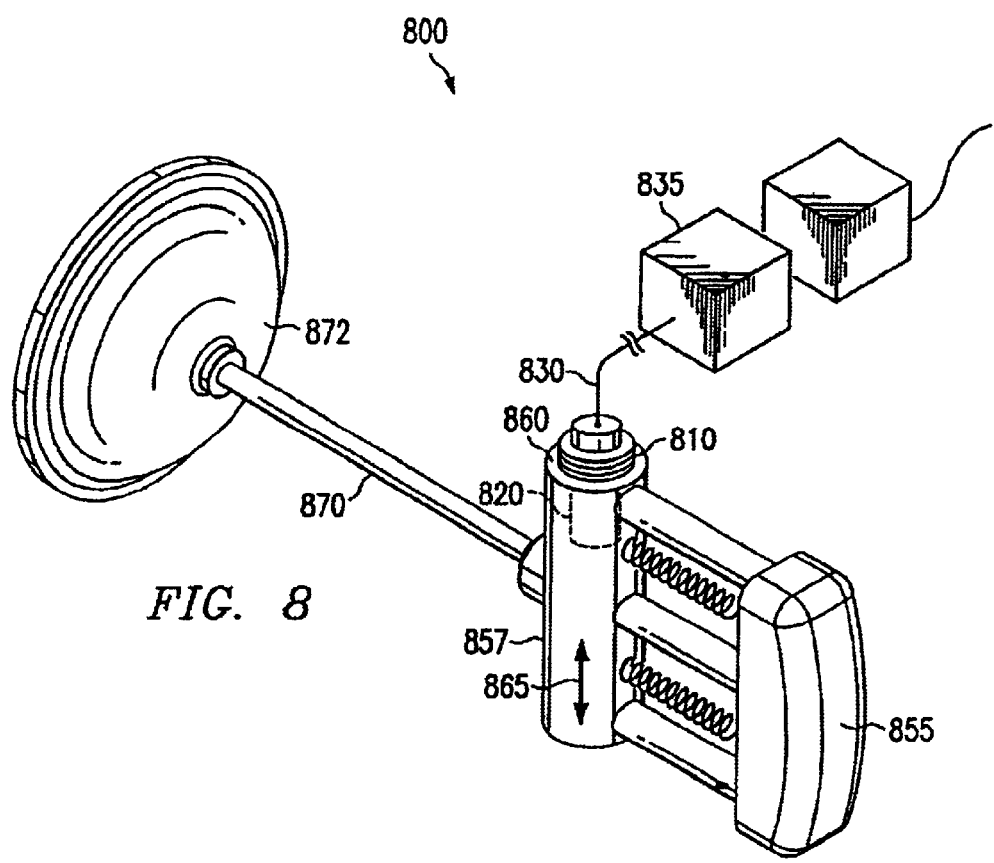
FIG. 8 illustrates a pump attachable device configured to attach to a hand pump, such as a KIWI hand pump.

FIG. 8 illustrates a pump attachable device 800 configured to attach to a hand pump 855, such as a KIWI hand pump. The pump attachable device 800 includes an adapter 810, such as threading, gaskets, or other attachments capable of forming a fluid-tight seal, a pressure-recording device 820, such as a transducer, and a cable 830 for communicating a detected pressure to a recording device via a plug 835. The hand pump 855 includes a handle 857 which maintains a vacuum cavity 865 therein. The vacuum cavity 865 is fluidly connected to a hose 870 and a suction device 872. The handle 857 also includes a pressure gauge receiver 860. In an unmodified hand pump, the pressure gauge receive 860 accepts a mechanical pressure gauge that mechanically indicate a detected pressure in the vacuum cavity 865. In the vacuum device according to the present embodiment of the invention, the pump attachable device 800 is secured into the handle 857 of the hand pump 855 via the pressure gauge 860.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

I claim:

1. A method of using a recording device that records a pressure in a vacuum device adapted for fetal obstetrics, the vacuum device enabled to couple to a fetus, comprising:

electronically detecting a pressure in the vacuum device, the vacuum device enabled to couple to a fetus;

electronically recording the pressure in real time; and storing a record of the pressure in the vacuum device.

2. The method of claim 1 wherein storing is achieved mechanically.

3. The method of claim 1 wherein storing is achieved electronically.

4. The method of claim 1 further comprising the act of generating a warning signal when a predetermined pressure is detected.

5. The method of claim 1 further comprising the act of altering the pressure to achieve a second pressure.

6. The method of claim 1 further comprising the act of releasing the pressure to achieve a local atmospheric pressure.

7. A method of using a recording device to record a pressure in a vacuum device adapted for fetal obstetrics, the vacuum device enabled to couple to a fetus, comprising:

placing the vacuum device on a fetus, the space between the fetus and the vacuum device having a pressure;

initiating a vacuum pressure in the suction device;

electronically detecting the vacuum pressure in the suction device; and automatically recording the vacuum pressure in real time.

8. A method of claim 7 further comprising the act of engaging a monitor.

9. The method of claim 7 further comprising the act of processing the recorded pressure to determine if the vacuum pressure is greater than a predetermined pressure.

10. The method of claim 9 further comprising the act of directing a change in the vacuum pressure.

11. The method of claim 10 wherein the change is an increase in the vacuum pressure to move the vacuum pressure closer to atmospheric pressure.

12. The method of claim 10 wherein the change is a release of the vacuum pressure in order to achieve an atmospheric pressure.

13. The method of claim 7 further comprising the act of altering the vacuum pressure in response to a direction to change the vacuum pressure.

14. The method of claim 7 further comprising the act of disengaging the vacuum pressure to achieve a local atmospheric pressure.

15. The method of claim 7 further comprising the act of removing the suction device from the fetus.

16. A method of using an electronic recording device to record a pressure in a vacuum device adapted for fetal obstetrics, the vacuum device enabled to couple to a fetus, comprising:

coupling the recording device to the vacuum device, the vacuum device enabled to couple to a fetus; and electronically recording the pressure in real time so that a record may be produced therefrom.

17. The method of claim 16 wherein the vacuum device comprises an electric pump.

18. The method of claim 16 wherein the vacuum device comprised a disposable electric pump.

* * * * *